United States Patent [19]
Davis

[11] Patent Number: 4,776,845
[45] Date of Patent: Oct. 11, 1988

[54] RECTAL-STOMAL INSERT APPARATUS

[76] Inventor: Emsley A. Davis, 1616 Colcord Ave., Waco, Tex. 76707

[21] Appl. No.: 879,332

[22] Filed: Jun. 27, 1986

[51] Int. Cl.⁴ .............................................. A61M 29/00
[52] U.S. Cl. ..................................... 604/96; 604/328; 604/45; 604/200; 128/4
[58] Field of Search ..................... 604/93, 328, 96–105, 604/264, 275, 277, 267, 278, 27, 35, 39, 41, 43, 45, 48, 200; 128/4

[56] References Cited

U.S. PATENT DOCUMENTS

| | | | |
|---|---|---|---|
| 2,922,415 | 9/1957 | Campagna | 128/4 |
| 3,421,509 | 1/1969 | Fiore | 604/200 |
| 4,117,847 | 10/1978 | Clayton | 604/328 |
| 4,381,765 | 5/1983 | Burton | 604/277 |
| 4,573,965 | 3/1986 | Russo | 604/45 |

FOREIGN PATENT DOCUMENTS 2079609 1/1982 United Kingdom .................. 604/45

*Primary Examiner*—C. Fred Rosenbaum
*Assistant Examiner*—Colleen M. Reilly
*Attorney, Agent, or Firm*—Arthur F. Zobal

[57] ABSTRACT

The rectal-stomal insert apparatus is used for occluding an opening in a patient's colon and preventing uncontrolled leakage during examination with a colonoscope. The apparatus includes an insertion member having an outer end, an inner end, and an exterior surface. The insertion member has an instrument channel and a separate and distinct suction channel each of which extends between the outer end and the inner end. The instrument channel is large enough to receive a colonoscope tube and is provided with a seal to seal around the colonoscope tube. An expandable occlusion member is coupled to the insertion member exterior surface. The occlusion member is made of a relatively soft material to sealingly engage and occlude the opening of the colon as the occlusion member is expanded. At the outer end of the suction channel is a longitudinal flange for receiving suction apparatus. A handle is provided at the outer end of the insertion member. Insertion aids having rounded ends and suitable lengths are provided for the channels to ease the insertion of the insertion member into the patient.

29 Claims, 4 Drawing Sheets

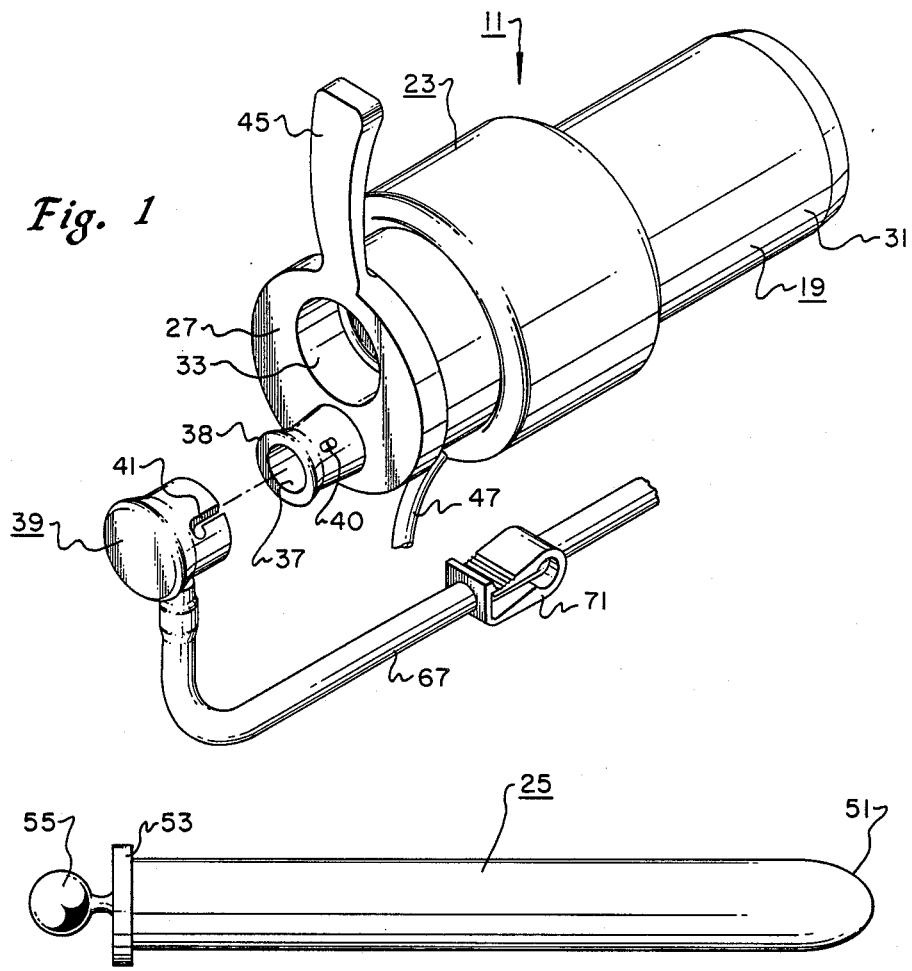
Fig. 1
Fig. 2
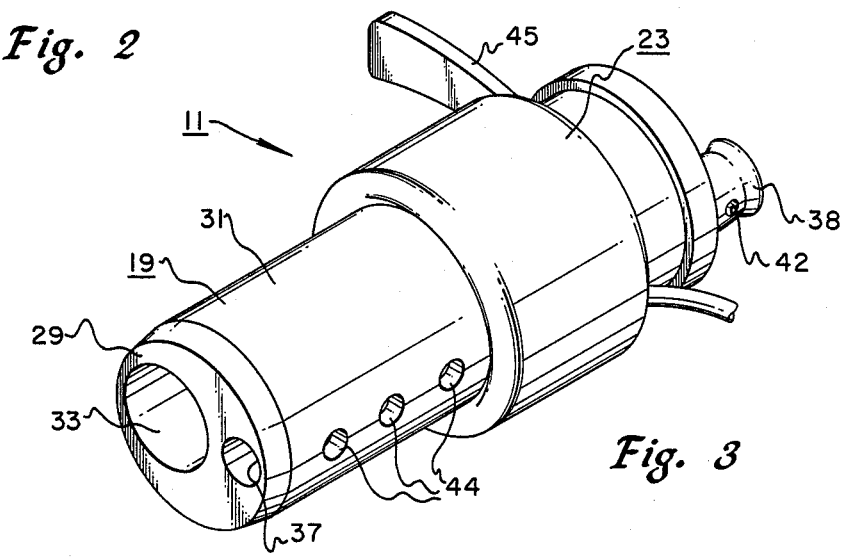
Fig. 3

4,776,845

RECTAL-STOMAL INSERT APPARATUS

FIELD OF THE INVENTION

The present invention relates to medical devices, particularly those devices that may be inserted into an opening of a patient.

BACKGROUND OF THE INVENTION

A colonoscopy is the visual examination of a patient's colon from a remote location through the use of instrumentation. In examining the colon, an instrument known as a colonoscope is used. The colonoscope is provided a sensing tube having optical means and insufflation means, and an observation and control unit that is connected to one end of the sensing tube. During the colonoscopy, the sensing tube is inserted into the colon via either the anus or a stoma in the patient's abdominal wall and the colon is inflated with the insufflation means to aid the surgeon's examination. In the past, surgeons have relied exclusively upon the sphincter muscles ringing the anus to provide a seal around the sensing tube. This seal is necessary to maintain the colon in an inflated condition and prevent the discharge of fecal material during the examination. However, the sphincter muscles relax after the administration of sedation and in older patients, thus reducing the seal around the colonoscope sensing tube and increasing the difficulty of the examination. In an examination through a stoma, there are no sphincter muscles to provide a seal.

SUMMARY OF THE INVENTION

It is an object of the present invention to provide an apparatus that will occlude an opening in a patient and prevent uncontrolled leakage through the opening during instrumenting.

The rectal-stomal insert apparatus of the present invention comprises an insertion member and an occlusion means. The insertion member has a longitudinal axis, an outer end, an inner end, and an exterior surface. The insertion member also has an instrument channel that extends between the outer and inner ends. The instrument channel is of suitable dimensions so it can receive the instrumentation to be inserted into the patient. The instrument channel has means for providing a seal around the instrumentation. The insertion member further has a suction channel that extends between the outer and inner ends and is separate and distinct from the instrument channel. The occlusion means is located around the exterior surface of the insertion member and can be inflated and deflated. When in use and inflated, the occlusion means engages the perimeter of the opening of the patient to form a seal between the exterior surface of the insertion member and the perimeter of the opening. The coupling means couples suction means to the outer end portion of the suction channel.

In a preferred embodiment of the invention, the insertion member exterior surface, the instrument channel, and the suction channel each is cylindrical in shape. The occlusion means comprises a toroidal shaped balloon. The coupling means comprises structure that extends longitudinally outward from the insertion member outer end. The wall structure of the insertion member has a plurality of apertures formed therethrough near the inner end to allow communication between the suction channel and the exterior of the insertion member. Handle means is coupled to the outer end of the insertion member and means for easing the insertion of the insertion member into the patient is provided. In the embodiment disclosed, the means for easing insertion comprises a cylindrical obturator or insertion aid for each channel. The insertion aids have rounded ends and suitable lengths so that when inserted into their respective channels, the rounded ends protrude from the insertion member inner end.

BRIEF DESCRIPTION OF THE DRAWINGS

FIG. 1 is an isometric view of a rectal-stomal insert apparatus of the present invention, in accordance with a preferred embodiment.

FIG. 2 is a plan view of an insertion aid.

FIG. 3 is an isometric view of the apparatus of FIG. 1 showing the inner end and the suction channel apertures.

DESCRIPTION OF A PREFERRED EMBODIMENT

Figure 4:
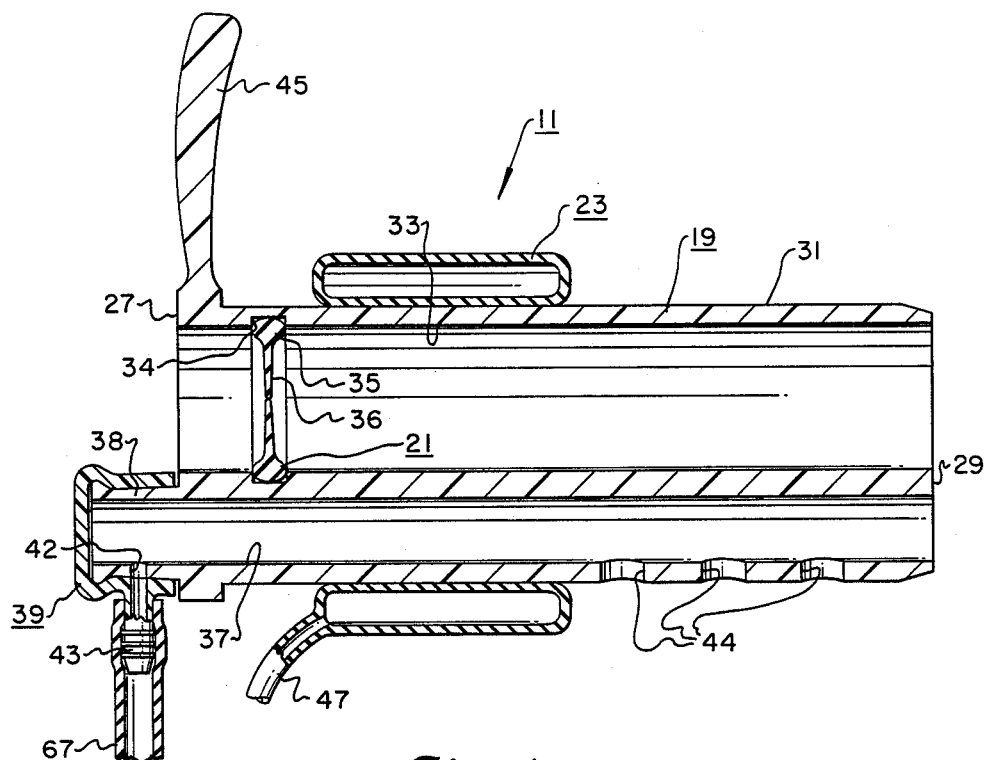
FIG. 4 is a longitudinal cross-sectional view of the apparatus of FIG. 1.

The rectal-stomal insert apparatus 11 described below is for use with a colonoscope 13 in visually examining a colon (see FIG. 7). A typical colonoscope 13 is provided a sensing tube 15 and an observation and control unit 17 to which the sensing tube is attached. The sensing tube 15 has optical sensory means for transmitting visual images to the observation and control unit 17 which is controlled by the operator. The sensing tube 15 also has insufflation means which is controlled by the operator at unit 17.

Referring to FIGS. 1–4, the rectal-stomal insert apparatus 11 of the present invention, in accordance with a preferred embodiment, comprises an insertion member 19 having a cylindrical instrument channel 33 and a cylindrical suction channel 37, an occlusion member 23, and insertion aids 25.

The insertion member 19 has a longitudinal axis, two ends, an outer end 27 and an inner end 29, and a smooth cylindrical exterior surface 31 connecting the two ends. The inner end portion of the exterior surface 31 is chamfered. The cylindrical instrument channel 33 is contained wholly within the exterior surface 31 and extends between the outer end 27 and the inner end 29 in a manner such that its axis is parallel to the insertion member longitudinal axis. Entry to the instrument channel 33 is obtained through the ends 27, 29. The instrument channel 33 is sized to receive the sensing tube 15 of the colonoscope. A circumferential groove 34 is located in the instrument channel 33 near the outer end and receives an instrument channel seal 21 formed of suitable flexible material such as an elastomer. The instrument channel seal 21 is circular with a thick ringlike outer portion 35 that fits into the circumferential groove 34 and a thinner inner portion 36 having a cruciate split to allow the passage of the colonoscope sensing tube 15.

The axis of the suction channel 37 is parallel to the instrument channel 33 and extends between the outer end 27 and the inner end 29. The suction channel 37 is, however, a separate and distinct channel from the instrument channel 33, there being no passageways between the two channels. At the outer end of the suction channel 37 is a flange or nipple 38 that extends longitudinally outward. The flange 38 forms a fitting for coupling suction means to the outer end portion of the suction channel 37. In the illustrated embodiment, the suction means includes a suction hose cap 39, a suction hose 67, and a clamp 71. The suction channel flange 38 is provided a pin 40 for engaging a slot 41 on the suction hose cap 39 and for locking the suction hose cap onto the suction channel flange. The suction channel flange 38 also has an exit aperture 42 that becomes aligned with the channel inside of the suction hose cap nipple 43 when the suction hose cap 39 is locked onto the suction channel flange. Apertures 44 penetrate the side wall of the suction channel 37 near the inner end portion of the channel allowing communication between the suction channel and the exterior of the member 19 and thus allowing alternate points of entry into the suction channel other than the opening at the inner end 29.

A handle 45 is provided on the outer end portion of the insertion member 19 and extends radially outward. In a preferred embodiment, the handle 45 is positioned on the insertion member 19 180° away from the suction channel apertures 44, to aid the operator in positioning the insertion member.

The occlusion member 23 is a toroidal shaped expandable balloon that is made of a relatively soft material such as an elastomer. The occlusion member 23 is coupled to the outer end portion of the insertion member exterior surface 31 with a suitable adhesive material. A filler tube 47 is integral with the occlusion member 23 and is provided with a syringe fitting 49 on its free end (see FIG. 6). As fluid is injected through the filler tube 47, the occlusion member 23 expands radially outward from the insertion member exterior surface 31. The occlusion member 23 may be made to contract by releasing fluid through the filler tube 47.

The plastic obturators or insertion aids 25, one of which is shown in FIG. 2, are cylindrical with one end 51 rounded and the other end having a stop in the form of a flange 53. A handle 55 extends longitudinally outward from the stop flange 53. There is an insertion aid 25 for each channel 33, 37 of the insertion member and each insertion aid is sized to fit within the respective instrument or suction channel. The insertion aids 25 are of a suitable length so that when inserted into their respective channels, the rounded ends 51 protrude from the inner end 29 of the insertion member and minimize the bluntness of the inner end.

Figure 5:
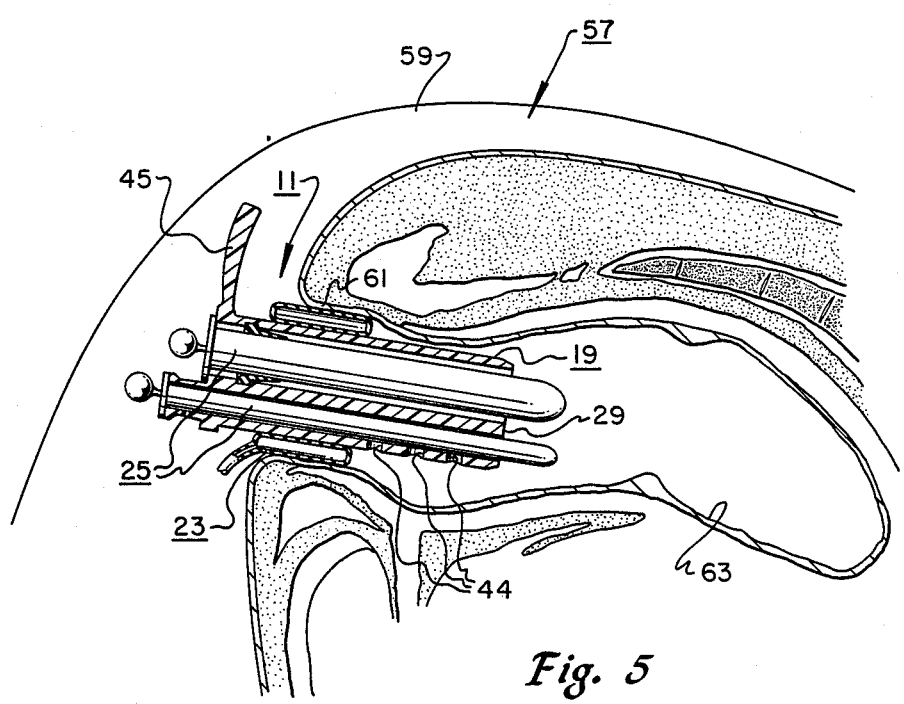
FIG. 5 is a longitudinal cross-sectional view of the apparatus of FIG. 1, inserted into the anorectal area of a patient.
Figure 6:
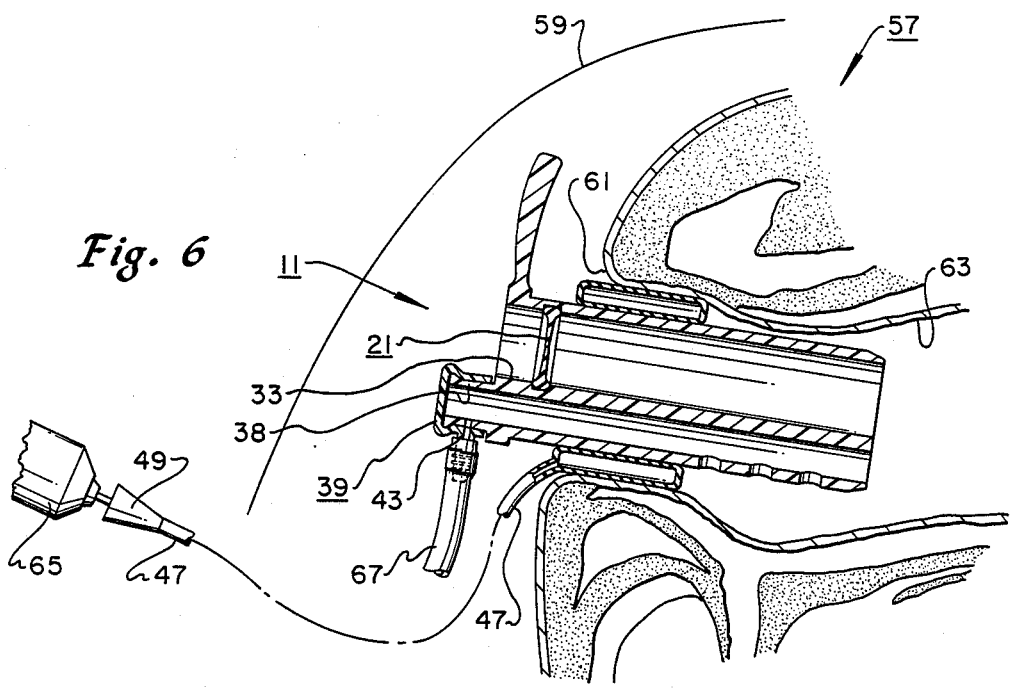
FIG. 6 is the same as FIG. 5, but shows the insertion aids removed.
Figure 7:
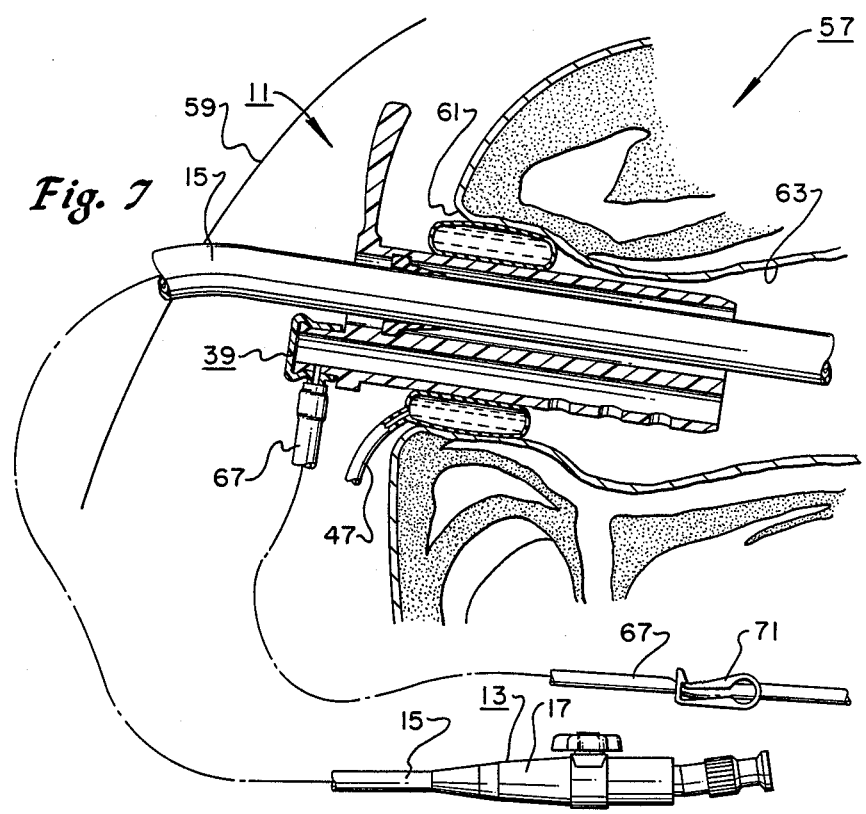
FIG. 7 is the same as FIG. 6, but shows a colonoscope sensing tube inserted into the apparatus and the occlusion member inflated.

Referring to FIGS. 5-7, the use of the rectal-stomal insert apparatus 11 will now be explained. In the figures, there are shown posterior portions of a human patient 57, including the buttocks 59, the anus 61, and the rectum 63. The insertion member 19 of the rectal-stomal insert apparatus 11 is inserted, inner end 29 first, into the anorectal area 61, 63 of the patient, after the insertion aids 25 have been placed into their respective channels 33, 37, all the way to the stop flanges 53 (see FIG. 5). The insertion aids 25 assist in preventing patient injury during the insertion of the apparatus 11 that might otherwise be caused by the bluntness of the inner end 29. The apparatus 11 is pushed into the rectum 63 sufficiently far enough such that the apertures 44 are all inside of the anorectal area and the occlusion member 23 is in contact with the anal tissue. The apparatus 11 should be oriented with the handle 45 pointed upward, thus causing the apertures 44 to be close to the bottommost portion of the rectum 63.

Once the apparatus 11 is properly positioned, the insertion aids 25 are removed and the occlusion member 23 is inflated with either a saline solution or air. A syringe 65 injects the fluid into the filler tube 47 at the syringe fitting 49 (see FIG. 6). As fluid is injected into the filler tube 47, the relatively soft occlusion member 23 expands against and sealingly engages the anal tissue to occlude the anus 61.

Next, a suction hose 67 is coupled to the nipple 43 of the suction hose cap 39 and the suction hose cap is locked onto the suction channel flange 38. The other end of the suction hose 67 is connected to a partial vacuum source such as is commonly available in hospitals. A clamp 71 for controlling the partial vacuum applied to the suction channel 37 is provided on the suction hose 67 in a convenient location: Then, the sensing tube 15 of the colonoscope 13 is inserted into the patient 57 through the instrument channel 33 and the actual examination commenced. In FIG. 7, the sensing tube 15 is shown at two different scales.

During the examination, the colon is inflated with the insufflation means provided in the sensing tube 15. Any uncontrolled leakage of the insufflation gas through the anus is prevented by the use of the apparatus 11 which fully occludes the anus 61. Seals are provided inside of the apparatus 11 by the instrument channel seal 21, which forms a seal around the colonoscope sensing tube 15, and outside of the apparatus by the inflated occlusion member 23.

In addition, any uncontrolled leakage of fecal material from the colon is prevented. Fecal material may be removed in a controlled manner from the rectum 63 through the suction channel 37 whenever a partial vacuum is applied to the channel. Removal of fecal material is enhanced by the plurality of apertures 44 which aid in maintaining suction and evacuation should the inner end of the suction channel 37 become blocked. The clamp 71 allows the control of the partial vacuum applied to the suction channel 37 to prevent constant actuation of the insufflation means and possible colon deflation during the examination.

Removal of the apparatus 11 from the patient 57 is accomplished by releasing fluid from the occlusion member 23, causing the occlusion member to contract, and then removing the injection member from the anorectal area.

Figure 8:
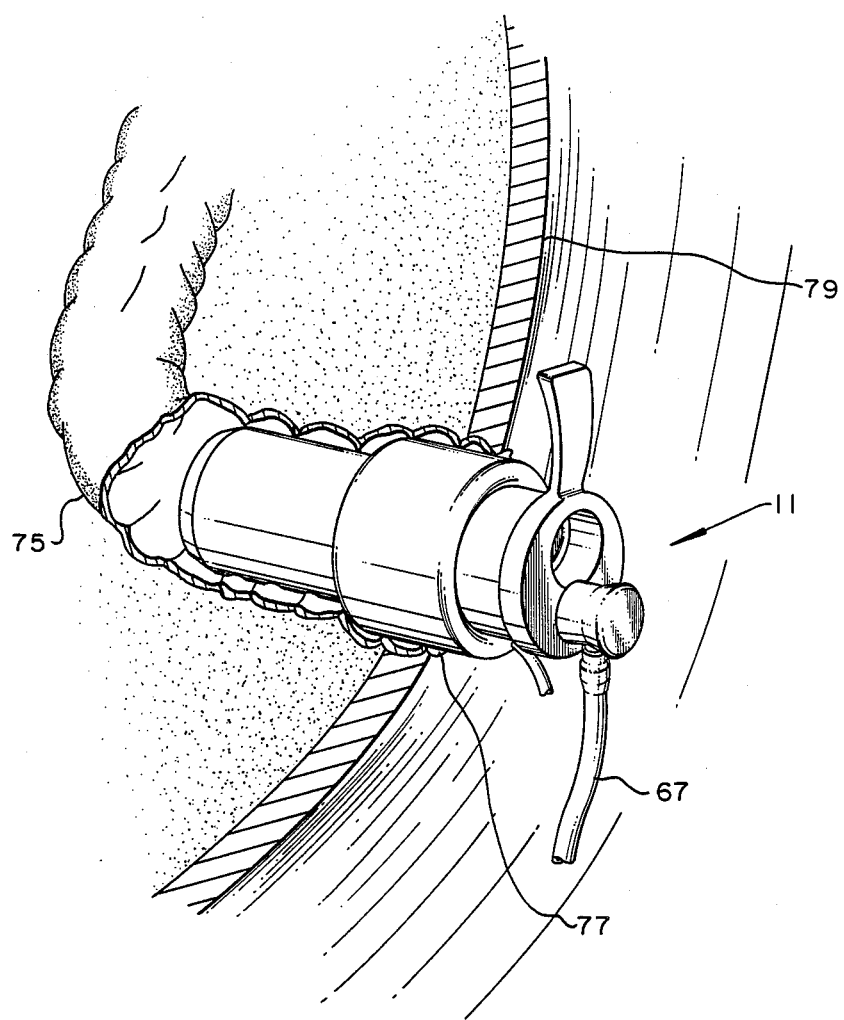
FIG. 8 shows the apparatus of FIG. 1 inserted into a colostomy.

The rectal-stomal insert apparatus 11 of the present invention may also be used to inspect a colon through a colostomy, as shown in FIG. 8. In a colostomy, the colon 75 has been surgically rerouted from the anus to a stoma 77 or opening in the abdomen 79. Unlike the anus, there are no sphincter muscles ringing the stoma 77 to assist in closing the stoma. Thus, the rectal-stomal insert apparatus is especially suited for use in occluding the stoma of a colostomy.

The foregoing disclosure and the showings made in the drawings are merely illustrative of the principles of this invention and are not to be interpreted in a limiting sense.

I claim:

1. An apparatus for insertion into an opening of the colon of a patient and for use with instrumentation to be inserted into the colon through said opening, comprising:

an insertion member having a longitudinal axis, an outer end portion, and an inner end portion, and having an exterior surface, said insertion member having an instrument channel extending between the outer end portion and the inner end portion, said instrument channel having suitable dimensions for receiving said instrumentation, and said instrument channel having means for providing a seal around said instrumentation, said insertion member having a suction channel extending between the outer end portion and the inner end portion, said suction channel being separate and distinct from said instrument channel, an occlusion member coupled to said exterior surface of said insertion member, said occlusion member being capable of expanding and contracting in a radial direction, said occlusion member being made of a relatively soft material to enable said occlusion member to sealingly engage the perimeter of said opening as said occlusion member expands, suction means coupled to the outer end portion of said suction channel, whereby the use of said apparatus during instrumenting occludes said opening and prevents uncontrolled leakage through said opening.

2. The apparatus of claim 1, wherein said insertion member exterior surface, said instrument channel, and said suction channel each is cylindrical in shape.

3. The apparatus of claim 2, wherein said occlusion member comprises a toroidal shaped balloon.

4. The apparatus of claim 2, comprising a plurality of apertures formed through the wall structure of said insertion member between the suction channel and the exterior surface of said insertion member at the inner end portion of said suction channel, said apertures allowing communication between said suction channel and the exterior of said insertion member.

5. The apparatus of claim 4, comprising handle means coupled to the outer end portion of said insertion member.

6. The apparatus of claim 4, comprising means for easing the insertion of said insertion member into said opening of said patient.

7. The apparatus of claim 6, wherein said means for easing the insertion of said insertion member comprises a removable cylindrical insertion aid for each channel of said insertion member, said insertion aids having rounded ends and suitable lengths so that when inserted into their respective channels, said rounded ends protrude from the inner end of said insertion member.

8. An apparatus for insertion into an opening of the colon of a patient and for use with instrumentation to be inserted into the colon through said opening, comprising:

an insertion member having an inner end to be inserted first into the opening, an opposite outer end, and an exterior surface, an instrument channel extending through said insertion member between said outer and inner ends for receiving instrumentation from said outer end which instrumentation may then be inserted through said instrument channel such that it projects beyond said inner end, a suction channel separate from said instrument channel formed through said insertion member between said outer and inner ends, said suction channel being adapted to have suction means coupled thereto at said outer end, occlusion means located around said insertion member for forming a seal between said exterior surface and the perimeter of said opening of the patient and seal means located in said instrument channel for forming a seal between the wall of said instrument channel and instrumentation to be inserted through said instrument channel.

9. The apparatus of claim 8, wherein:
said occlusion means comprises inflatable means adapted to be inflated and deflated.

10. The apparatus of claim 9, wherein:
said inflatable means comprises a toroidal shaped balloon means.

11. The apparatus of claim 8, comprising:
a plurality of apertures formed through the wall structure of said insertion member between the suction channel and the exterior surface of said insertion member near said inner end for allowing fluid communication between said suction channel near said inner end and the exterior of said insertion member.

12. The apparatus of claim 8, comprising:
a removable insertion aid for each channel adapted to be inserted through its channel from said outer end, each of said insertion aids having a rounded end and a length such that when inserted through its channel, its rounded end protrudes from the inner end of said insertion member.

13. The apparatus of claim 12, comprising:
a plurality of apertures formed through the wall structure of said insertion member between the juction channel and the exterior surface of said insertion member near said inner end for allowing fluid communication between said suction channel near said inner end and the exterior of said insertion member.

14. An apparatus for insertion into an opening of the colon of a patient and for use with instrumentation to be inserted into the colon through the opening, comprising:

an insertion member having an inner end to be inserted first into the opening of the colon of a patient, an opposite outer end, and an exterior surface, an instrument channel extending through said insertion member between said outer and inner ends for receiving instrumentation from said outer end which instrumentation may then be inserted through said instrument channel such that it projects beyond said inner end, a suction channel separate from said instrument channel formed through said insertion member between said outer and inner ends, said suction channel being adapted to have suction means coupled thereto at said outer end, and occlusion means located around said insertion member between said inner and outer ends for forming a seal between said exterior surface and the perimeter of the opening of the colon of the patient, said occulusion member being located at a position spaced from said inner and outer ends whereby said inner and outer ends extend beyond opposite ends respectively of said occulsion member.

15. The apparatus of claim 14, wherein:
said occlusion member comprises as expandable member adapted to be expanded radially outward to engage the perimeter of the opening of the colon of a patient for sealing purposes.

16. The apparatus of claim 14, comprising:
a plurality of apertures formed through the wall structure of said insertion member between the suction channel and the exterior surface of said insertion member,
said plurality of apertures being located between said occulsion member and said inner end.

17. The apparatus of claim 14, comprising:
flexible seal means located in said instrument channel for forming a seal between the wall of said instrument channel and instrumentation to be inserted through said instrument channel,
said flexible seal means being secured to the wall of said instrument channel and extending radially inward such that it normally occupies a substantial part of the cross-sectional area of said instrment channel in a given plane,
said flexible seal means comprising structure which may be moved by instrumentation to allow passage of the instrumentation through the central portion of said flexible seal means.

18. The apparatus of claim 15, comprising:
flexible seal means located in said instrument channel for forming a seal between the wall of said instrument channel and instrumentation to be inserted through said instrument channel.
said flexible seal means being secured to the wall of said instrument channel and extending radially inward such that is normally occupies a substantial part of the cross-sectional area of said instrument channel in a given plane,
said flexible seal means comprising structure which may be moved by instrumentation to allow passage of the instrumentation through the central portion of said flexible seal means.

19. The apparatus of claim 14, wherein:
said exterior surface of said insertion member from said inner end to a position near said outer end is generally cylindrical in shape,
the wall of said instrument channel is generally cylindrical in shape,
an annular flexible seal means secured to the wall of said instrument channel and extending radially inward for forming a seal between the wall of said instrument channel and instrumentation to be inserted through said instrument channel,
said suction channel is spaced to one side of said instrument channel and is substantially straight along its entire length.

20. The apparatus of claim 15, wherein:
said exterior surface of said insertion member from said inner end to a position near said outer end is generally cylindrical in shape,
the wall of said instrument channel is generally cylindrical in shape,
an annular flexible seal means secured to the wall of said instrument channel and extending radially inward for forming a seal between the wall of said instrument channel and instrumentation to be inserted through said instrument channel,
said suction channel is spaced to one side of said instrument channel and is substantially straight along its entire length.

21. The apparatus of claim 20, wherein:
said flexible seal means normally occupies a substantialy part of the cross-sectional area of said instrument channel in a given plane,
said flexible seal means comprising structure which may be moved by instrumentation to allow passage of the instrumentation through the central portion of said flexible seal means.

22. The apparatus of claim 21, comprising:
handle means coupled to said outer end of said insertion member.

23. The apparatus of claim 22, comprising:
a removable insertion aid for each channel adapted to be inserted through its channel from said outer end,
each of said insertion aids having a rounded end and a length such that when inserted through its channel, its rounded end protrudes from said inner end of said insertion member.

24. An apparatus for insertion into an opening of the colon of a patient and for use with instrumentation to be inserted into the colon through the opening, comprising:
an insertion member having an inner end to be inserted first into the opening of the colon of a patient, an opposite outer end, and an exterior surface,
an instrument channel extending through said insertion member between said outer and inner ends for receiving instrumentation from said outer end which instrumentation may then be inserted through said instrument channel such that it projects beyond said inner end,
a suction channel separate from said instrument channel formed through said insertion member between said outer and inner ends,
said suction channel being adapted to have suction means coupled thereto at said outer end,
said exterior surface of said insertion member from said inner end to a position near said outer end being generally cylindrical in shape,
the wall of said instrument channel being generally cylindrical in shape,
an annular flexible seal means secured to the wall of said instrument channel and extending radially inward for forming a seal between the wall of said instrument channel and instrumentation to be inserted through said instrument channel,
said suction channel being spaced to one side of said instrument channel and being substantially straight along its entire length, and
occulsion means located around said insertion member for forming a seal between said exterior surface and the perimeter of the opening of the colon of the patient.

25. The apparatus of claim 24, wherein:
said flexible seal means normally occupies a substantial part of the cross-sectional area of said instrument channel in a given plane,
said flexible seal means comprising structure which may be moved by instrumentation to allow passage of the instrumentation through the central portion of said flexible seal means.

26. The apparatus of claim 25, comprising:
handle means coupled to said outer end of said insertion member.

27. The apparatus of claim 26, comprising:
a removable insertion aid for each channel adapted to be inserted through its channel from said outer end, each of said insertion aids having a rounded end and a length such that when inserted through its channel, its rounded end protrudes from said inner end of said insertion member.

28. The apparatus of claim 14, comprising:
seal means coupled to said insertion member for forming a seal between the wall of said instrument channel and instrumentation to be inserted through said instrument channel.

29. The apparatus of claim 28, wherein:
said seal means is secured to the wall of said instrument channel and extends inward into said instrument channel.

* * * * *